United States Patent [19]

Soula

[11] 4,287,125
[45] Sep. 1, 1981

[54] PREPARATION OF BENZENOID ETHERS AND THIOETHERS

[75] Inventor: Gerard Soula, Meyzieu, France

[73] Assignee: Rhone-Poulenc Industries, Paris, France

[21] Appl. No.: 161,512

[22] Filed: Jun. 20, 1980

[30] Foreign Application Priority Data

Jun. 27, 1979 [FR] France ................. 79 16544

[51] Int. Cl.$^3$ ............. C07C 41/01; C07C 65/21; C07C 79/35; C07C 121/75

[52] U.S. Cl. ............. 260/340.9 R; 568/39; 568/41; 260/465 R; 568/42; 568/44; 260/465 D; 568/45; 568/49; 260/465 E; 568/51; 568/53; 260/465 F; 568/55; 568/56; 260/465 G; 568/57; 568/58; 260/505 R; 568/306; 568/424; 260/507 R; 568/584; 568/585; 260/508; 568/586; 568/587; 260/509; 568/588; 568/637; 260/511; 568/639; 568/642; 260/512 R; 568/643; 568/645; 260/512 C; 568/647; 560/18; 560/21; 560/23; 560/37; 560/45; 560/64; 560/65; 562/432; 562/435; 562/437; 562/438; 562/473; 562/474; 564/162; 564/166; 564/169; 564/171; 564/430; 568/33; 568/38

[58] Field of Search ........... 260/571, 340.9 R, 465 D, 260/465 E, 465 F, 465 G, 465 R, 505 R, 508, 509, 511, 512 R, 512 C; 560/18, 21, 23, 45, 64, 65; 562/432, 435, 437, 438, 473, 474; 564/162, 166, 169, 171, 430; 568/33, 38, 39, 41, 42, 44, 45, 49, 51, 53, 55, 56, 57, 58, 306, 424, 584, 585, 586, 587, 588, 637, 639, 642, 643, 645, 647

[56] References Cited

U.S. PATENT DOCUMENTS

3,032,594 5/1962 Towle ........................ 568/585
3,763,210 10/1973 Heath et al. ................. 260/465 F

FOREIGN PATENT DOCUMENTS

1302365 7/1962 France .

*Primary Examiner*—Dolph H. Torrence
*Attorney, Agent, or Firm*—Burns, Doane, Swecker & Mathis

[57] ABSTRACT

Benzenoid ethers/thioethers are prepared by reacting an activated halobenzene with an anionic reactant, $RA^-M^+$, in the presence of at least one tertiary amine sequestering agent having formula:

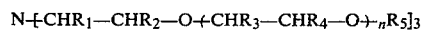

N-[CHR$_1$—CHR$_2$—O-(CHR$_3$—CHR$_4$—O)$_n$R$_5$]$_3$

22 Claims, No Drawings

PREPARATION OF BENZENOID ETHERS AND THIOETHERS

CROSS-REFERENCE TO RELATED APPLICATIONS (i) Soula and Linguenheld application, Ser. No. 148,590, filed May 12, 1980, and assigned to the assignee hereof; and (ii) Soula and Michelet application, Ser. No. 161,516, filed June 20, 1980, also assigned to the assignee hereof.

BACKGROUND OF THE INVENTION

1. Field of the Invention

The present invention relates to an improved process for the preparation of aryl ethers and thioethers, and, more especially, to a process for the preparation of benzenoid ethers and thioethers by reacting an activated halobenzene with an anionic, organic oxygen-containing or sulfur-containing reactant.

By the term "activated halobenzene" as utilized herein, there is intended a halobenzene containing an electron-attracting group in the ortho- or para-position to the halogen, and by the term "anionic, organic oxygen-containing or sulfur-containing reactant" there is intended a reactant of the type $RO^-M^+$ or $RS^-M^+$, R being a hydrocarbon radical.

2. Description of the Prior Art

Known to the art is a process for the preparation of compounds of the general formula $A-Y-A'-Z_n$, in which A and A' represent substituted or unsubstituted aryl radicals, Z is an electron-attracting group and Y is O, S or $SO_2$, n being between 1 and 3. In accordance with this process, described in French Application No. 76/13,943 (U.S. Pat. No. 2,311,004), a compound of the formula A-YMe, in which Me represents an alkali metal or $NH_4$, is reacted with a compound of the formula $X-A-Z_n$, in which X is a halogen or an activated nitro group.

The reaction is carried out in a two-phase system, one of the phases being water or an alkaline aqueous medium, in which the compound A-YMe is reacted, and the other consisting of a solution of the compound $X-A'-Z_n$ in one or more water-immiscible solvents. The reaction is carried out in the presence of quaternary ammonium or phosphonium derivatives as catalysts.

The main disadvantages of this type of process are associated with the use of an aqueous phase. The presence of water mandates operation under pressure when the reaction temperature is above 100° C. Furthermore, it involves the use of water-immiscible solvents which do not form emulsions with water in the presence of quaternary ammonium derivatives. Yet, some reactions only take place with appreciable yields when using aprotic polar solvents, such as sulfolane, dimethylsulfoxide and N-methylpyrrolidone, which are water-miscible solvents. It too will be appreciated that the large amount of water required, as is apparent from the examples in the abovementioned French patent application, makes it necessary to employ large reactors.

Further disadvantages result from the use of quaternary ammonium or phosphonium derivatives as catalysts. In fact, those skilled in the art are well aware that such catalysts easily degrade when exposed to temperatures above about 130° C. Furthermore, serious difficulties are encountered, from an industrial point of view, in separating the catalyst from the reaction product.

An additional disadvantage of this type of prior art process lies in the fact that it does not permit the use of alcoholates which degrade in the presence of water.

SUMMARY OF THE INVENTION

Accordingly, a major object of the present invention is the provision of an improved process for the preparation of benzenoid ethers and thioethers by reacting an activated halobenzene with an anionic, organic oxygen-containing or sulfur-containing reactant, in the absence of water, and which process conveniently avoids those drawbacks and disadvantages above outlined.

Another object of the invention is to provide an improved process which can be conducted in the presence of a catalyst which does not degrade at elevated temperature.

Yet another object of the invention is to provide an improved process which permits of the easy separation and recovery of the catalyst from the reaction medium.

Briefly, the present invention features a process for the preparation of benzenoid ethers and thioethers by reacting an activated halobenzene with an anionic, organic oxygen-containing or sulfur-containing reactant, characterized in that the reaction is conducted in the presence of at least one sequestering agent having the structural formula:

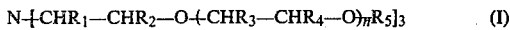

$$N\text{-}[CHR_1-CHR_2-O\text{-}(CHR_3-CHR_4-O)_mR_5]_3 \qquad (I)$$

in which n is an integer which is greater than or equal to 0 and less than or equal to about 10 ($0 \leq n \leq 10$), $R_1$, $R_2$, $R_3$ and $R_4$, which are identical or different, each represent a hydrogen atom or an alkyl radical having from 1 to 4 carbon atoms, and $R_5$ represents an alkyl or cycloalkyl radical having from 1 to 12 carbon atoms, a phenyl radical or a radical $-C_mH_{2m}-\phi$ or $C_mH_{2m+1}-\phi-$, in which m ranges from 1 to 12 ($1 \leq m \leq 12$).

The subject reaction can be carried out either in the presence or absence of a solvent. If no auxiliary solvent is used, it is the activated halobenzene itself which serves as the solvent.

DETAILED DESCRIPTION OF THE INVENTION

More particularly according to this invention, it has now been determined that the sequestering agent of the formula (I) forms, with the anionic, organic oxygen-containing or sulfur-containing reactant, a complex which is soluble in solvents in which the anionic, organic oxygen-containing or sulfur-containing reactant is insoluble, or is very sparingly soluble in the uncomplexed state. It will be apparent that, as a result of the immediately aforesaid, the process according to the invention enables employing solvents, the use of which was not heretofore technically feasible. This is all the more advantageous because it becomes possible to use solvents which are much easier to handle on an industrial scale than the solvents previously used. A further advantage of the invention is that, although not yet completely understood in detail, it would appear that the complexation due to the sequestering agent of the formula (I) itself activates the reaction system.

According to a preferred embodiment of the invention, a sequestering agent of the formula (I) is used in which $R_1$, $R_2$, $R_3$ and $R_4$ represent a hydrogen atom or a methyl radical, $R_5$ and n being as above defined.

Among such sequestering agents, it is even more particularly preferred to employ those in which n is greater than or equal to 0 and less than or equal to 6 and in which R₅ represents an alkyl radical having from 1 to 4 carbon atoms.

The following sequestering agents are noted as illustrative:

[1] tris-(3-oxabutyl)-amine of the formula:

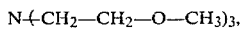
N—(CH₂—CH₂—O—CH₃)₃,

[2] tris-(3,6-dioxaheptyl)-amine of the formula:

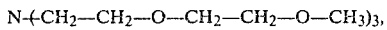
N—(CH₂—CH₂—O—CH₂—CH₂—O—CH₃)₃,

[3] tris-(3,6,9-trioxadecyl)-amine of the formula:

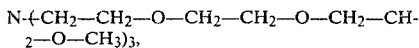
N—(CH₂—CH₂—O—CH₂—CH₂—O—CH₂—CH₂—O—CH₃)₃,

[4] tris-(3,6-dioxaoctyl)-amine of the formula:

N—(CH₂—CH₂—O—CH₂—CH₂—O—C₂H₅)₃,

[5] tris-(3,6,9-trioxaundecyl)-amine of the formula:

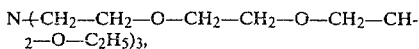
N—(CH₂—CH₂—O—CH₂—CH₂—O—CH₂—CH₂—O—C₂H₅)₃,

[6] tris-(3,6-dioxanonyl)-amine of the formula:

N—(CH₂—CH₂—O—CH₂—CH₂—O—C₃H₇)₃,

[7] tris-(3,6,9-trioxadodecyl)-amine of the formula:

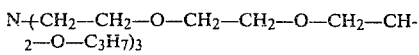
N—(CH₂—CH₂—O—CH₂—CH₂—O—CH₂—CH₂—O—C₃H₇)₃

[8] tris-(3,6-dioxadecyl)-amine of the formula:

N—(CH₂—CH₂O—CH₂—CH₂—O—C₄H₉)₃,

[9] tris-(3,6,9-trioxatridecyl)-amine of the formula:

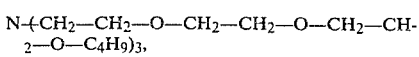
N—(CH₂—CH₂—O—CH₂—CH₂—O—CH₂—CH₂—O—C₄H₉)₃,

[10] tris-(3,6,9,12-tetraoxatridecyl)-amine of the formula:

N—[CH₂—CH₂—O—(CH₂—CH₂O)₃CH₃]₃,

[11] tris-(3,6,9,12,15,18-hexaoxanonadecyl)-amine of the formula:

N—[CH₂—CH₂—O—(CH₂—CH₂—O—)₅CH₃]₃,

[12] tris-(3,6-dioxa-4-methylheptyl)-amine of the formula:

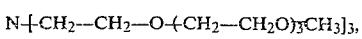
N—[CH₂—CH₂—O—CH(CH₃)—CH₂—O—CH₃]₃
and

[13] tris-(3,6-dioxa-2,4-dimethylheptyl)-amine of the formula:

N—[CH₂—CH(CH₃)—O—CH(CH₃)CH₂—O—CH₃]₃.

The amine sequestering agent utilized in the process according to the invention are per se known to the prior art. Thus, French Pat. No. 1,302,365 describes the preparation of the tertiary amines N—CH₂—CH₂—O—CH₃)₃ and N—CH₂—CH₂—O—CH₂—CH₂—O—CH₃)₃ as by-products from the synthesis of the corresponding primary and secondary amines, such primary and secondary amines being valuable as intermediates in the synthesis of pharmaceuticals, as corrosion inhibitors, as intermediates in the synthesis of chemical products of value in agriculture, and as emulsifiers. It will also be appreciated, though, that the prior art, including the aforenoted French Pat. No. 1,302,365, is conspicuously devoid of any suggestion that the topic amines could be utilized in any reaction within the ambit of this invention.

Characteristic activated halobenzenes reacted in accordance with the process of the invention have the structural formula:

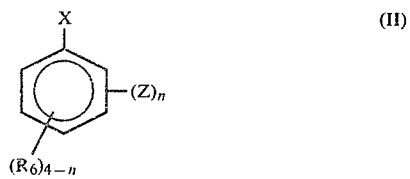

(II)

in which X represents a halogen atom (F, Cl, Br or I), Z represents at least one electron-attracting group selected from the group comprising NO₂, CN, SO₃M, CO₂M and CF₃, in which M represents an alkali metal, Z being located in the ortho- and/or para-position to the group X, R₆ represents at least one substituent selected from the group comprising:

hydrogen, alkyl and cycloalkyl radicals having from 1 to 12 carbon atoms, alkenyl radicals having from 3 to 12 carbon atoms, such as, for example, propenyl, nonyl and dodecyl radicals, the radicals of the formulae $C_mH_{2m+1}$—φ—, $C_mH_{2m-1}$—φ— and φ—$C_mH_{2m}$—, in which m is an integer ranging from 1 to 12 (1≦m≦12) and in which the phenyl moiety φ can either be substituted or unsubstituted, alkoxy radicals having from 1 to 12 carbon atoms and phenoxy radicals, the radicals —$C_mH_{2m}$—OH and —$C_mH_{2m}$OR, in which m is an integer ranging from 1 to 12 (1≦m≦12) and in which R is an alkyl radical having from 1 to 12 carbon atoms or a phenyl radical, alkylthio radicals having from 1 to 12 carbon atoms and phenylthio radicals, the radicals $C_pH_{2p+1-q}F_q$, p ranging from 1 to 4 (1≦p≦4) and q ranging from 3 to 9 (3≦p≦9), such as, for example, —CF₃ and —CH₂—CF₃, the radicals

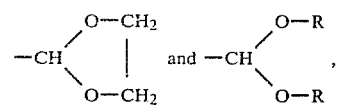

in which R is an alkyl radical having from 1 to 12 carbon atoms or a phenyl radical, the radicals Cl, F and Br, and the radicals —NO₂, —SO₃M, —CN, —CO₂M, —CO₂R, —COR and —COH, in which M represents an alkali metal and in which R represents an alkyl radical having from 1 to 12 carbon atoms or a phenyl radical, and n is an integer which can be equal to 1, 2 or 3 ($1 \leq n \leq 3$).

The anionic oxygen-containing or sulfur-containing reactants employed in the process of the invention have the structural formula:

$$R_7 - A^- M^+ \qquad (III)$$

in which $R_7$ represents a radical selected from the group comprising linear or branched chain alkyl radicals and cycloalkyl radicals which have from 1 to 12 carbon atoms and are optionally substituted, and optionally substituted aryl radicals having from 6 to 10 carbon atoms, A represents oxygen or sulfur and $M^+$ represents a monovalent or divalent cation comprising an alkali metal or alkaline earth metal, or the ammonium cation $NH_4^+$.

The compounds of the formula III to which the process according to the invention more particularly, but not exclusively, applies are those in which $R_7$ represents a radical selected from the group comprising linear or branched chain alkyl radicals and cycloalkyl radicals which have from 1 to 6 carbon atoms and are optionally substituted, and phenyl and naphthyl radicals which are optionally substituted by at least one of the following radicals: alkyl radicals having from 1 to 6 carbon atoms, phenyl radicals, halo, nitro, cyano, amido and amino radicals, alkoxy radicals having from 1 to 6 carbon atoms, phenoxy radicals, alkylamino radicals having from 1 to 6 carbon atoms, phenylamino radicals, alkylamido radicals having from 1 to 6 carbon atoms and phenylamido radicals.

The following compounds are exemplary of the compounds of the formula II:

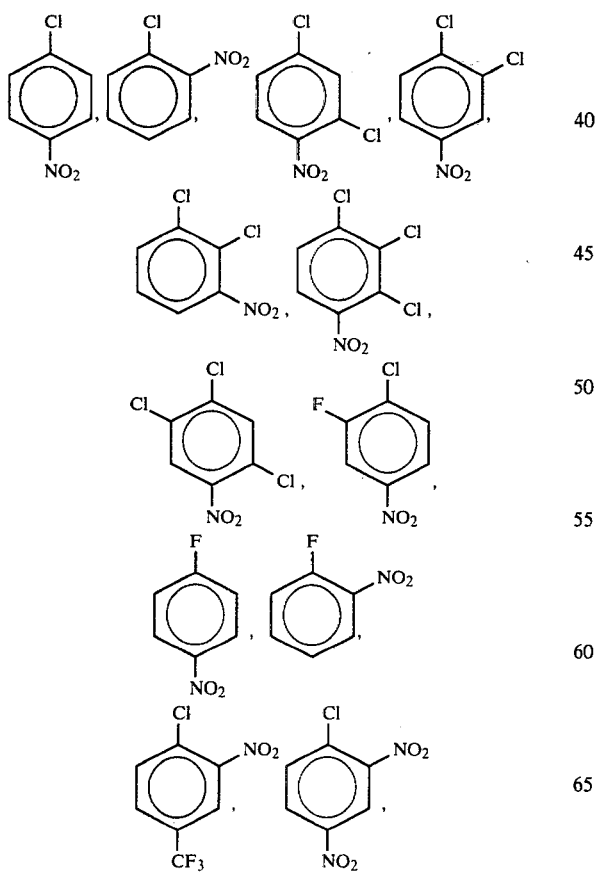

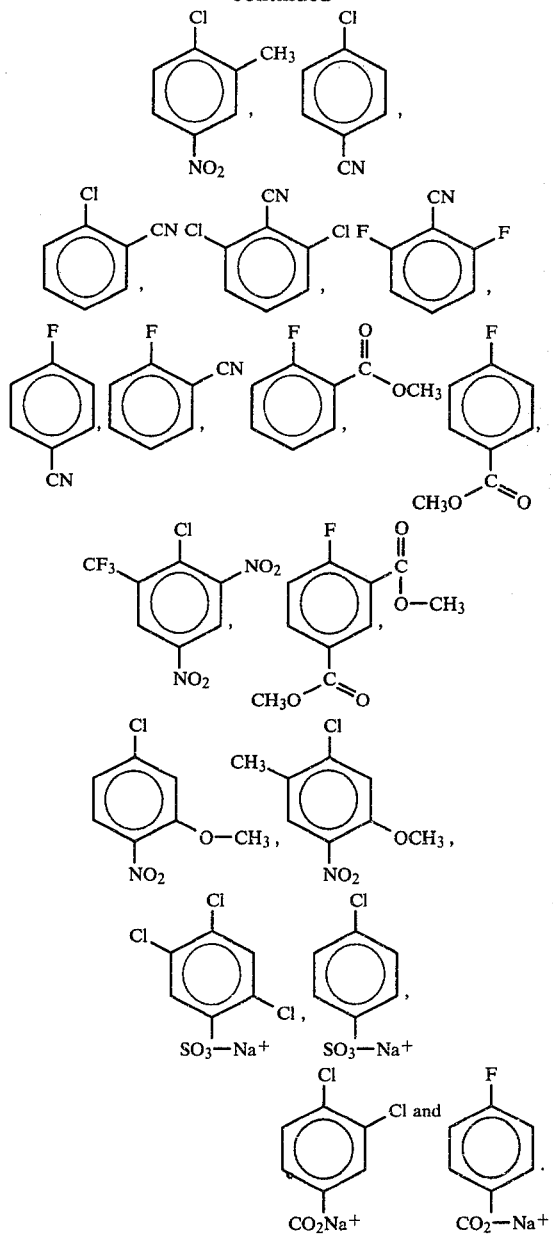

Exemplary of compounds of the formula III are the alkali metal or ammonium salts of the following compounds: alcohols, such as methanol, ethanol, isopropanol and butanol, cyclic alcohols, such as cyclohexanol and furfurol, phenols, such as phenol, alkylphenols, such as o-, p- and m-cresol, 2-isopropyl-4-methylphenol and 2-isopropyl-5-methylphenol, dodecylphenol and nonylphenol, arylphenols, such as paraphenylphenol, monohalophenols, such as o-, p- and m-chlorophenol and the corresponding bromo, iodo and fluoro compounds, polyhalophenols, such as dichlorophenols, trichlorophenols, tetrachlorophenols and pentachlorophenol, "mixed" dihalophenols, such as 3-chloro-4-bromophenol, 3-chloro-4-fluorophenol, 3-chloro-5-fluorophenol and equivalent compounds, haloalkylphenols, such as 3-trifluoromethylphenol and 4-trifluoromethylphenol, alkylhalophenols, such as 2-methyl-4-chlorophenol and 2, 4-dimethyl-5-chlorophenol, aminophenols, such as 3-aminophenol, 4-aminophenol, 2-methyl- 4-aminophenol and 2-(N,N-dimethylamino)phenol, cyanophenols, such as 2-cyanophenol and 4-cyanophenol, nitrophenols, such as o-, p- and m-nitrophenol, 2-methyl-3-nitrophenol, 2-methyl-4-nitrophenol and 2,4-dinitrophenol, amidophenols, such as o-, p- and m-amidophenol, alkoxyphenols, such as 3-methoxyphenol, 2-methoxyphenol and 4-methoxyphenol, phenoxyphenols, such as o-, m- and p-phenoxyphenol, alkylamidophenols, such as 2-dimethylamidophenol, thioalcohols, such as methylmercaptan and ethylmercaptan, thiophenols, such as p-chlorothiophenol, p-aminothiophenol, 2-methylthiophenol, 3-methylthiophenol, 4-methylthiophenol and 2,4-dimethylthiophenol, and mercaptobenzothiazoles.

The selection of the most suitable sequestering agent for carrying out the process according to the invention is made with regard to the size of the cation M+ (compound of the formula III). The larger the cation, the larger must be the number of oxygen atoms present in the molecule of the sequestering agent. Thus, if a potassium phenolate is used, it is preferred to use tris-(3,6,9-trioxadecyl)-amine, whereas tris-(3,6-dioxaheptyl)-amine is preferred in the case of the corresponding sodium salt.

The auxiliary solvent, if such a solvent is used, must satisfy a certain number of conditions; firstly, it must solubilize the sequestering agent (the latter is soluble in the majority of customary solvents); secondly, it must be chemically inert vis-a-vis the salts to be dissolved. It must also be noted that, in order to achieve the best results from the process according to the invention, the more marked the apolar character of the solvent chosen, the more marked must be the lipophilic character of the sequestering agent (namely, the greater must be the number of carbon atoms present in the sequestering agent).

Examples of the auxiliary solvents which can be used are acetonitrile, N-methylpyrrolidone, chlorobenzene, o-dichlorobenzene, dimethysulfoxide, diphenyl ether, dioxane and ethylene glycol polyethers (commonly referred to as "glymes").

The compounds II and III can be used in stoichiometric amounts or in excess relative to the stoichiometric amount. According to a preferred embodiment, a 20% excess is used, relative to the stoichiometry of one or the other of the compounds II and III.

The amount of the amine of the formula I employed can be between about 1 and about 100 mols per 100 mols of the compound of the formula III. It is preferred to use between 1 and 15 mols of amine per 100 mols of compound III.

If an auxiliary solvent is used, it is employed in an amount such that it contains from about 10 to 500% of its weight of the compound of the formula III.

The process according to the invention is carried out at a temperature between about 50° C. and about 200° C., preferably between about 80° C. and about 160° C.

The pressure is not critical. The process is generally carried out under atmospheric pressure, although lower or higher pressures are not excluded.

The compounds prepared in accordance with the process of the invention have the following general formulae IV:

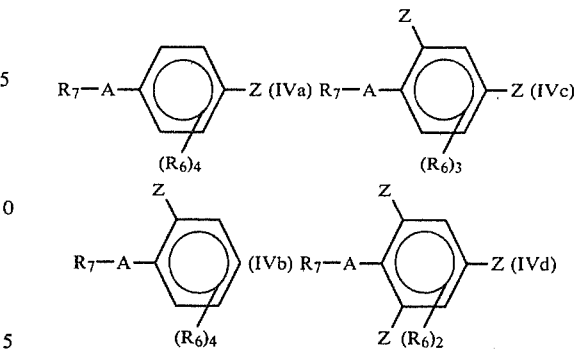

in which $R_6$, $R_7$, A and Z are as above defined.

The following compounds are exemplary of the compounds corresponding to one of the formulae IVa–d:

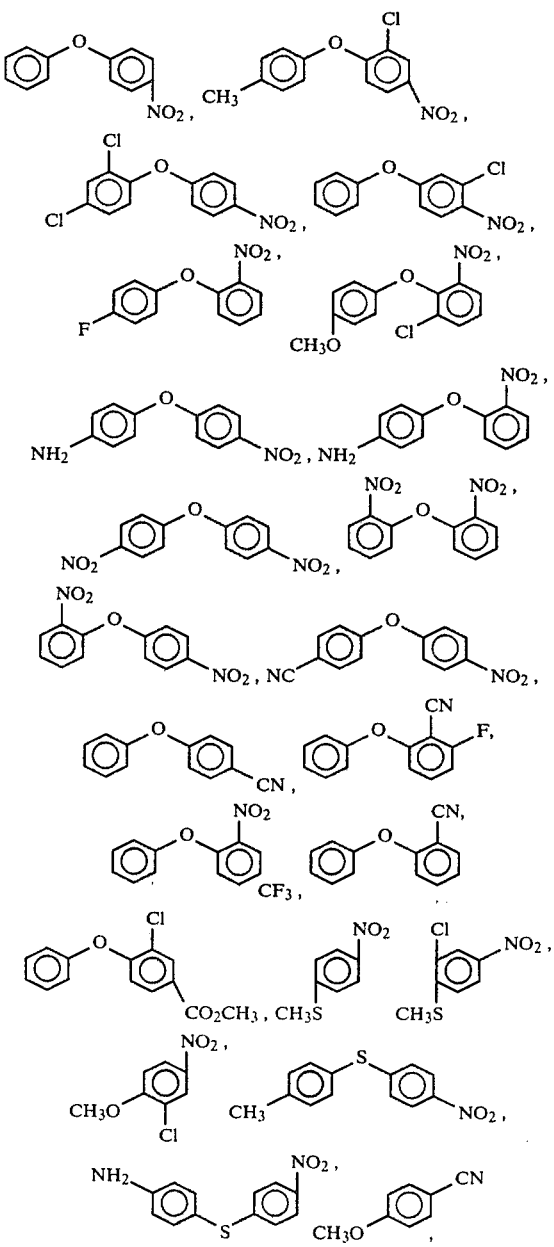

-continued

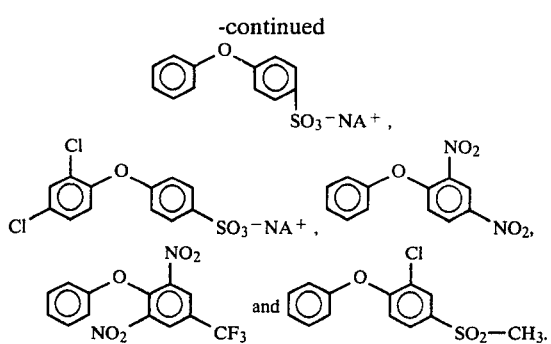

The subject compounds are notable intermediates for the synthesis of organic compounds which can be used as plantprotection agents.

The sequestering agents of the formula I employed in the process according to the invention can be prepared by condensing a salt of the formula:

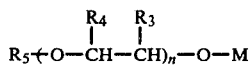

in which $R_3$, $R_4$, $R_5$ and n are as above defined and in which M represents an alkali metal atom selected from among sodium, potassium and lithium, either with an amine of the general formula:

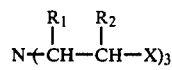

in which $R_1$ and $R_2$ are as above defined and X represents chlorine or bromine, or with the corresponding hydrochloride or hydrobromide.

The molar ratio alkali metal salt/amine is between about 3 and about 5.

The condensation is carried out at a temperature between 100° and 150° C. for 1 to 15 hours, in the presence of a solvent which can be, for example, chlorobenzene or, preferably, the ethylene glycol monoalkyl ether of the formula $R_5—(O—CHR_4—CHR_3)_n—OH$.

The process is preferably carried out in such fashion that the solution contains from 2 to 5 mols of alkali metal salt per liter of solvent.

The mixture upon completion of the reaction essentially consists of the tertiary amine of the formula:

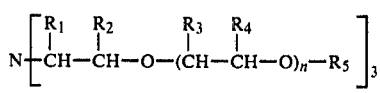

but also contains a small proportion of the corresponding secondary amine:

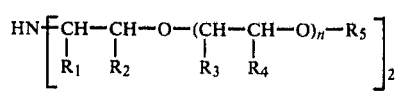

and traces of the primary amine:

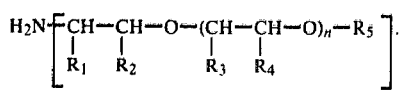

The tertiary, secondary and primary amines are typically present in the ratio 90:8:2, respectively, after distillation.

In the process according to the invention, the above mixture obtained after a first distillation, namely, containing the three types of amine, can be used directly.

In order to achieve better results consistent with the invention, it is preferred to carry out a more thorough distillation of the above mixture in order to obtain an essentially pure tertiary amine.

In order to further illustrate the present invention and the advantages thereof, the following specific examples are given, it being understood that same are intended only as illustrative and in nowise limitative.

EXAMPLE 1

Reaction of $\phi O^-Na^+$ with para-nitrochlorobenzene, in order to prepare para-phenoxynitrobenzene having the structural formula:

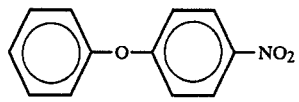

in the presence of tris-(3,6-dioxaheptyl)-amine in dichlorobenzene.

100 cm³ of chlorobenzene, 32 g (0.2 mol) of para-nitrochlorobenzene, 23 g (0.2 mol) of sodium phenate and 3.7 g (0.01 mol) of tris-(3,6-dioxaoctyl)-amine were successively introduced into a 500 ml three-necked round-bottomed flask equipped with a mechanical stirrer, a thermometer and a reflux condenser. The mixture was stirred and heated at 130° C. for 9 hours. The yield of the reaction was 95% in respect of the para-phenoxynitrobenzene isolated.

COMPARATIVE EXAMPLE

Under the same operating conditions as above, but in the absence of tris-(3,6-dioxaoctyl)-amine, the yield of the reaction was 3%.

EXAMPLE 2

Reaction of sodium 2, 4-dichlorophenate having the formula:

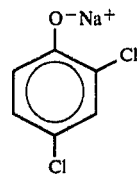

with para-nitrochlorobenzene, in order to prepare para-(2,4-dichlorphenoxy)-nitrobenzene having the formula:

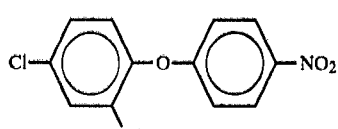

in the presence of tris-(3,6-dioxaheptyl)-amine in dichlorobenzene.

100 cm³ of monochlorobenzene, 15.7 g (0.1 mol) of para-chloronitrobenzene, 27.8 g (0.16 mol) of sodium 2,4-dichlorophenate and 2.3 g (0.007 mol) of tris-(3,6-dioxaheptyl)-amine were successively introduced into a 500 ml three-necked round-bottomed flask equipped with a mechanical stirrer, a thermometer and a reflux condenser. The mixture was stirred and heated at the reflux temperature of the chlorobenzene for 12 hours. The yield of the reaction was 68%.

COMPARATIVE EXAMPLE

In the absence of tris-(3,6-dioxaheptyl)-amine, but otherwise conducting the reaction as above, the yield was 8%.

EXAMPLE 3

Reaction of potassium para-nitrophenate having the formula:

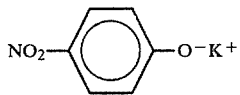

with para-fluoronitrobenzene, in order to prepare 4,4'-dinitrodiphenyl ether having the formula:

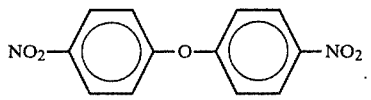

in the presence of tris-(3,6,9-trioxadecyl)-amine in o-dichlorobenzene.

200 cm³ of ortho-dichlorobenzene, 14.1 g (0.1 mol) of para-fluoronitrobenzene, 17.7 g (0.1 mol) of potassium para-nitrophenated and 4.55 g (0.01 mol) of tris-(3,6,9-trioxadecyl)-amine were successively introduced into a 500 ml three-necked round-bottomed flask equipped with a mechanical stirrer, a thermometer and a reflux condenser. The mixture was stirred and heated at the reflux temperature of the ortho-dichlorobenzene for 10 hours. The yield of the reaction was 87%.

EXAMPLE 4

Reaction of potassium para-nitrophenate with ortho-nitrofluorobenzene having the formula:

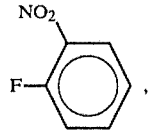

in order to prepare 2,4'-dinitrodiphenyl ether having the formula:

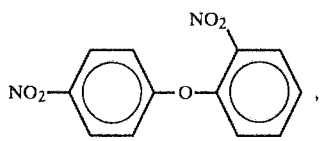

in the presence of tris-(3,6,9-trioxadecyl)-amine in ortho-dichlorobenzene.

200 cm³ of ortho-dichlorobenzene, 14.1 g (0.1 mol) of ortho-fluoronitrobenzene, 17.7 g (0.1 mol) of potassium para-nitrophenate and 4.55 g (0.01 mol) of tris-(3,6,9-trioxadecyl)-amine were successively introduced into a 500 ml three-necked round-bottomed flask equipped with a mechanical stirrer, a thermometer and a reflux condenser. The mixture was stirred and heated at the reflux temperature of the ortho-dichlorobenzene for 10 hours. After cooling, the salts were removed and the solvent was then evaporated off. The yield of the reaction was 85%.

EXAMPLE 5

Reaction of potassium ortho-nitrophenate having the formula:

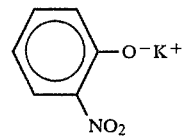

with ortho-nitrofluorbenzene, in order to prepare 2,2'-dinitrodiphenyl ether having the formula:

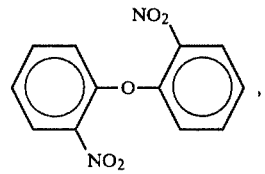

in the presence of tris-(3,6,9-trioxadecyl)-amine in o-dichlorobenzene.

200 cm³ of ortho-dichlorobenzene, 14.1 g (0.1 mol) of ortho-fluoronitrobenzene, 17.7 g (0.1 mol) of potassium ortho-nitrophenate and 4.55 g (0.01 mol) of tris-(3,6,9-trioxadecyl)-amine were successively introduced into a 500 ml three-necked round-bottomed flask equipped with a mechanical stirrer, a thermometer and a reflux condenser. The mixture was stirred and heated at the reflux temperature of the ortho-dichlorobenzene for 8 hours. After cooling the salts were removed and the solvent was then evaporated off. The yield of the reaction was 82%.

EXAMPLE 6

Reaction of sodium para-aminophenate with para-nitrochlorobenzene, in order to prepare para-(4-aminophenoxy)-nitrobenzene having the formula:

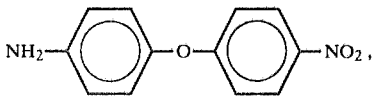

in the presence of tris-(3,6-dioxaheptyl)-amine in chlorobenzene.

100 cm³ of chlorobenzene, 15.7 g (0.1 mol) of para-chloronitrobenzene, 13.1 g (0.1 mol) of sodium para-aminophenate and 1.6 g (0.005 mol) of tris-(3,6-dioxaheptyl)-amine were successively introduced into a 500 ml three-necked round-bottomed flask equipped with a mechanical stirrer, a thermometer and a reflux condenser. The mixture was stirred and heated at 130° C. for 13 hours and the resulting solution was then filtered hot. After filtration, 300 cm³ of hexane were added and this effected the precipitation of the para-(4-aminophenoxy)-nitrobenzene. The yield of the reaction was 83%.

EXAMPLE 7

Reaction of sodium thiomethylate having the formula: $CH_3S^-Na^+$ with para-nitrochlorobenzene, in order to prepare para-thiomethoxynitrobenzene having the formula:

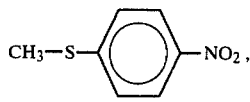

in the presence of tris-(3,6-dioxaheptyl)-amine in chlorobenzene.

1-liter of chlorobenzene, 157 g (1 mol) of para-nitrochlorobenzene, 140 g (2 mols) of sodium thiomethylate and 32 g (0.1 mol) of tris-(3,6-dioxaheptyl)-amine were successively introduced into a 2 liter three-necked round-bottomed flask equipped with a mechanical stirrer, a thermometer and a reflux condenser. The mixture was stirred and heated for 2 hours at the reflux temperature of the chlorobenzene and then cooled. The salts formed, and also the unconverted sodium thiomethylate, were removed by filtration and the chlorobenzene was evaporated off. The thiomethoxynitrobenzene was distilled. The yield of the reaction was 72%.

EXAMPLE 8

Reaction of potassium phenate with para-chlorobenzonitrile, in order to prepare para-phenoxybenzonitrile having the formula:

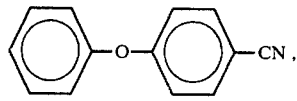

in the presence of tris-(3,6,9-trioxadecyl)-amine in o-dichlorobenzene.

200 cm³ of ortho-dichlorobenzene, 27.5 g (0.2 mol) of para-chlorobenzonitrile, 29.04 g (0.22 mol) of potassium phenate and 4.55 g (0.01 mol) of tris-(3,6,9-trioxadecyl)-amine were successively introduced into a 500 ml three-necked round-bottomed flask equipped with a mechanical stirrer, a thermometer and a reflux condenser. The reaction mixture was stirred and heated at the reflux temperature of the ortho-dichlorobenzene for 8 hours. The salts formed were removed by filtration and the solvent was removed by distillation. The yield of the reaction was 85%.

COMPARATIVE EXAMPLE

Under the same operating conditions as above, but in the absence of tris-(3,6,9-trioxadecyl)-amine, the yield was only 3%.

EXAMPLE 9

Reaction of sodium phenate with 3-nitro-4-chlorotrifluoromethylbenzene, in order to prepare 3-mitro-4-phenoxytrifluoromethylbenzene having the formula:

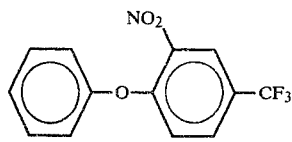

in the presence of tris-(3,6-dioxaheptyl)-amine in chlorobenzene.

200 cm³ of chlorobenzene, 22.5 g (0.1 mol) of 3-nitro-4-chlorotrifluoromethylbenzene, 13 g (0.11 mol) of sodium phenate and 3.2 g (0.01 mol) of tris-(3,6-dioxaheptyl)-amine were successively introduced into a 500 ml three-necked round-bottomed flask equipped with a mechanical stirrer, a thermometer and a reflux condenser.

The mixture was stirred and heated at the reflux temperature of the chlorobenzene for 4 hours. After cooling, the salts were filtered off and the solvent was then evaporated off. The yield of the reaction was 92%.

COMPARATIVE EXAMPLE

In the absence of tris-(3,6-dioxaheptyl)-amine, but otherwise conducting the reaction as above, the yield of the reaction was 18%.

EXAMPLE 10

Preparation of tris-(3,6-dioxaheptyl)-amine:

(a) 380 g (5 mols) of 2-methoxyethanol were introduced into a one liter three-necked round-bottomed flask fitted with a mechanical stirrer, and a thermometer and a condenser. 23 g (1 mol) of sodium were added over the course of 3 hours, while maintaining the temperature of the mixture at 40° C.

(b) 51.6 g (namely, 0.215 mol) of tris-(2-chloroethyl)-amine hydrochloride were added to the above mixture. The mixture was subsequently heated at the reflux temperature of the 2-methoxyethanol (125° C.) for 12 hours and the solvent was then distilled under reduced pressure. The excess sodium 2-methoxyethanolate was neutralized by adding 11.6 cm³ of aqueous HCl (10 N). The sodium chloride was filtered off and the solution was distilled.

EXAMPLE 11

Preparation of tris-(3,6,9-trioxadecyl)-amine:

600 g, namely, 5 mols, of diethylene glycol monomethyl ether (3,6-dioxaheptan-1-ol) were introduced into a 1 liter three-necked round-bottomed flask equipped with a mechanical stirrer, a condenser and a thermometer, and 23 g (1 mol) of sodium were then introduced in small portions in order to form sodium 3,6-dioxaheptanolate.

When the sodium had been totally converted, 51.8 g (namely, 0.215 mol) of tris-(2-chloroethyl)-amine hydrochloride were added. The mixture was heated at 130° C. for 8 hours, under stirring, and then cooled, and the excess sodium alcoholate was neutralized with a 10% strength aqueous solution of hydrochloric acid. The 3,6-dioxaheptan-1-ol was removed by distillation at 130° C. under a pressure of 20 mm Hg. The resulting mixture was filtered in order to remove the sodium chloride, and the product was then distilled. 83 g of tris-(3.6.9-trioxadecyl)-amine, which distilled at 189° C. under a pressure of 0.1 mm Hg, were thus obtained.

The other sequestering agents within the scope of the present invention are prepared in similar manner.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What is claimed is:

1. A process for the preparation of a benzenoid ether or thioether, comprising reacting an activated halobenzene with the anionic reactant, $RA^-M^+$, wherein R is a hydrocarbon, A is oxygen or sulfur, and M is alkali or alkaline earth metal, or ammonium, in the presence of at least one tertiary amine sequestering agent having the formula:

$$N\text{-}[CHR_1\text{---}CHR_2\text{---}O\text{-}(CHR_3\text{---}CHR_4\text{---}O)_nR_5]_3 \quad (I)$$

in which n is an integer which is greater than or equal to 0 and less than or equal to about 10, $R_1$, $R_2$, $R_3$ and $R_4$, which are identical or different, each represent a hydrogen atom or an alkyl radical having from 1 to 4 carbon atoms and $R_5$ represents an alkyl or cycloalkyl radical having from 1 to 12 carbon atoms, a phenyl radical or a radical $-C_mH_{2m}-\phi$ or $C_mH_{2m+1}-\phi-$, wherein $\phi$ is phenyl and in which m ranges from 1 to 12.

2. The process as defined in claim 1, wherein the formula (I), $R_1$, $R_2$, $R_3$ and $R_4$ are each hydrogen or methyl.

3. The process as defined by claim 2, wherein the formula (I), n is an integer which is greater than or equal to 0 and less than or equal to 6.

4. The process as defined by claims 2 or 3, wherein the formula (I), $R_5$ is an alkyl radical having from 1 to 4 carbon atoms.

5. The process as defined by claim 1, wherein the formula (I), $R_1$, $R_2$, $R_3$ and $R_4$, which are identical or different, are each hydrogen or methyl, n is an integer which is greater than or equal 0 and less than or equal to 6 and $R_5$ is an alkyl radical having from 1 to 4 carbon atoms.

6. The process as defined by claim 5, wherein the tertiary amine of the formula (I) is tris-(3,6-dioxaheptyl)-amine of the formula:

$$N-(CH_2-CH_2-O-CH_2-CH_2-O-CH_3)_3.$$

7. The process as defined by claim 5, wherein the tertiary amine of the formula (I) is tris-(3,6,9-trioxadecyl)-amine of the formula:

$$N-(CH_2-CH_2-O-CH_2-CH_2-O-CH_2-CH_2-O-CH_3)_3.$$

8. The process as defined by claim 5, wherein the tertiary amine of the formula (I) is tris-(3,6-dioxaoctyl)-amine of the formula:

$$N-(CH_2-CH_2-O-CH_2-CH_2O-C_2H_5)_3.$$

9. The process as defined by claim 1, wherein the tertiary amine of the formula (I) is selected from the group consisting of tris-(3-oxabutyl)-amine, tris-(3,6-dioxaheptyl-amine, tris-(3,6,9-trioxadecyl)-amine, tris-(3,6-dioxaoctyl)-amine, tris-(3,6,9-trioxaundecyl)-amine, tris-(3,6-dioxanonyl)-amine, tris(3,6,9-trioxadodecyl)-amine, tris-(3,6-dioxadecyl)-amine, tris-(3,6,9-trioxatridecyl)-amine, tris-(3,6,9,12-tetraoxatridecyl)-amine, tris-(3,6,9,12,15,18-hexaoxanonadecyl)-amine, tris-(3,6-dioxa-4-methylheptyl-amine and tris-(3,6-dioxa-2,4-dimethylheptyl)-amine.

10. The process as defined by claim 1, wherein the reaction is conducted in the presence of an inert organic solvent, under anhydrous conditions.

11. The process as defined by claim 10, said solvent being selected from the group consisting of acetonitrile, chlorobenzene, o-dichlorobenzene, diphenyl ether, dioxane, ethylene glycol polyether, N-methylpyrrolidone and dimethylsulfoxide.

12. The process as defined by claims 1 or 10, wherein the reactant $RA^-M^+$, A is oxygen.

13. The process as defined by claims 1 or 10, wherein the reactant $RA^-M^+$, A is sulfur.

14. The process as defined by claims 1 or 10, wherein the activated halobenzene reacted has the structural formula:

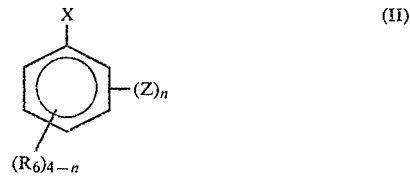

in which X represents a halogen atom, (F, Cl, Br or I), Z represents at least one electron-attracting group selected from the group consisting of $NO_2$, $CN$, $SO_3M$, $CO_2M$ and $CF_3$, in which M represents an alkali metal, Z is in the ortho- and/or para-position to the group X, $R_6$ represents at least one substituent selected from the group consisting of hydrogen, alkyl and cycloalkyl radicals having from 1 to 12 carbon atoms, alkenyl radicals having from 3 to 12 carbon atoms, the radicals of the formulae $C_mH_{2m+1}-\phi-$, $C_mH_{2m-1}-\phi-$ and $\phi-C_mH_{2m}-$, in which m is an integer ranging from 1 to 12 and $\phi$ comprises a phenyl moiety, alkoxy radicals having from 1 to 12 carbon atoms and phenoxy radicals, the radicals $-C_mH_{2m}-OH$ and $C_mH_{2m}OR$, in which m is an integer ranging from 1 to 12 and in which R is an alkyl radical having from 1 to 12 carbon atoms or a phenyl radical, alkylthio radicals having from 1 to 12 carbon atoms and phenylthio radicals, the radicals $C_pH_{2p+1-q}F_q$, p ranging from 1 to 4 and q ranging from 3 to 9, the radicals

in which R is an alkyl radical having from 1 to 12 carbon atoms or a phenyl radical, the radicals Cl, F and Br, and the radicals $-NO_2$, $-SO_3M$, $-CN$, $-CO_2M$, $-CO_2R$, $-COR$ and $-COH$, in which M represents an alkali metal and in which R represents an alkyl radical having from 1 to 12 carbon atoms or a phenyl radical, and n is an integer which can be equal to 1, 2 or 3.

15. The process as defined by claim 14, wherein the anionic reactant has the structural formula:

$$R_7-A^-M^+ \quad (III)$$

in which $R_7$ represents a radical selected from the group consisting of substituted or unsubstituted linear or branched chain alkyl radicals and cycloalkyl radicals which have from 1 to 12 carbon atoms, substituted or unsubstituted aryl radicals having from 6 to 10 carbon atoms, $A^-$ represents oxygen or sulfur, and $M^+$ represents a monovalent or divalent cation selected from the group consisting of an alkali metal or alkaline earth metal, or the ammonium cation $NH_4^+$.

16. The process as defined by claim 15, in which $R_7$ represents a radical selected from the group consisting of linear or branched chain alkyl radicals and cycloalkyl radicals which have from 1 to 6 carbon atoms and substituted such radicals, and phenyl and naphthyl radicals and substituted such radicals, said substituents being selected from the group consisting of alkyl radicals having from 1 to 6 carbon atoms, phenyl radicals, halo, nitro, cyano, amido and amino radicals, alkoxy radicals having from 1 to 6 carbon atoms, phenoxy radicals, alkylamino radicals having from 1 to 6 carbon atoms, phenylamino radicals, alkylamido radicals having from 1 to 6 carbon atoms and phenylamido radicals.

17. The process as defined by claims 1 or 10, wherein the molar ratio of the sequestering agent (I) to the anionic reaction ranges from 1/100 to 1/1.

18. The process as defined by claim 17, wherein said molar ratio ranges from 1/100 to 15/100.

19. The process as defined by claim 17, said solvent comprising from 10 to 500% by weight thereof, of the anionic reactant.

20. The process as defined by claim 19, the reaction being conducted in the presence of an about 20% stoichiometric excess of either the activated halobenzene or the anionic reactant.

21. The process as defined by claim 19, wherein the reaction is conducted at a temperature of from about 50° C. to 200° C.

22. The process as defined by claim 21, wherein the reaction is conducted at a temperature of from about 80° C. to 160° C.

* * * * *